US012630644B2

(12) United States Patent
Du et al.

(10) Patent No.:  US 12,630,644 B2
(45) Date of Patent:       May 19, 2026

(54) ANTI-CD40 SINGLE-DOMAIN ANTIBODY, AND PREPARATION METHOD THEREFOR AND USE THEREOF

(71) Applicant: BIOINTRON BIOLOGICAL INC., Shanghai (CN)

(72) Inventors: Jiwen Du, Shanghai (CN); Jing Xue, Shanghai (CN); Yan Yang, Shanghai (CN); Yafeng Yuan, Shanghai (CN); Yinhui Xu, Shanghai (CN); Hui Ding, Shanghai (CN); Yufang Wang, Shanghai (CN); Changchun Zha, Shanghai (CN)

(73) Assignee: BIOINTRON BIOLOGICAL INC., Shanghai (CN)

( * ) Notice: Subject to any disclaimer, the term of this patent is extended or adjusted under 35 U.S.C. 154(b) by 0 days.

(21) Appl. No.: 19/017,195

(22) Filed: Jan. 10, 2025

(65) Prior Publication Data

US 2025/0188180 A1      Jun. 12, 2025

Related U.S. Application Data

(63) Continuation of application No. PCT/CN2023/077183, filed on Feb. 20, 2023.

(30) Foreign Application Priority Data

Sep. 5, 2022    (CN) .......................... 202211078773.2

(51) Int. Cl.
*C07K 16/28*       (2006.01)
*G01N 33/53*       (2006.01)

(52) U.S. Cl.
CPC ......... *C07K 16/2878* (2013.01); *G01N 33/53* (2013.01); *C07K 2317/565* (2013.01); *C07K 2317/569* (2013.01); *G01N 2333/70578* (2013.01)

(58) Field of Classification Search
None
See application file for complete search history.

(56) References Cited

U.S. PATENT DOCUMENTS

| | | | | | |
|---|---|---|---|---|---|
| 9,475,879 | B2 * | 10/2016 | Suri | .......................... | A61P 19/00 |
| 11,220,550 | B2 * | 1/2022 | Yamniuk | ................. | A61P 37/00 |
| 2016/0311916 | A1 | 10/2016 | Ellmark | | |
| 2021/0155705 | A1 | 5/2021 | Yang et al. | | |
| 2022/0135694 | A1 | 5/2022 | Van Der Vliet et al. | | |

* cited by examiner

*Primary Examiner* — Claire Kaufman
(74) *Attorney, Agent, or Firm* — George D. Morgan

(57) ABSTRACT

The present invention relates to the technical field of molecular biology, and in particular, to an anti-CD40 nanobody, and a preparation method therefor and use thereof. The anti-CD40 nanobody provided by the present invention has three unique complementarity determining regions, namely CDR1, CDR2, and CDR3. The present invention further provides a sequence encoding the nanobody or its VHH chain, a corresponding expression vector, and a host cell capable of expressing the nanobody. The present invention includes immunizing an alpaca by constructing a CD40 antigen to obtain a PBMC of the alpaca and constructing a vector; screening an anti-CD40 antibody through phage display; and finally obtaining a highly sensitive and specifically binding antibody through functional assays and sequencing result analysis. The nanobody provided by the present invention can specifically recognize and bind to CD40.

4 Claims, 5 Drawing Sheets

Specification includes a Sequence Listing.

- ◆ ANb24-Alpaca1-4M-2SP-149
- ■ ANb24-Alpaca1-4M-2SP-175
- ✦ ANb24-Alpaca1-4M-2SP-180
- ✦ ANb24-Alpaca1-4M-2SP-226
- ✦ ANb24-Alpaca1-4M-2SP-273
- ● ANb24-Alpaca1-4M-2SP-317
- ■ ANb24-Alpaca1-4M-2SP-332
- ▲ ANb24-Alpaca1-4M-2SP-335

1

ANTI-CD40 SINGLE-DOMAIN ANTIBODY, AND PREPARATION METHOD THEREFOR AND USE THEREOF

CROSS-REFERENCE TO RELATED APPLICATIONS

The application claims priority to Chinese patent application No. 202211078773.2, filed on Sep. 5, 2022, the entire contents of which are incorporated herein by reference.

SEQUENCE LISTING

The sequence listing xml file submitted herewith, named "NEW-ANTI_CD40_sequence_listing.xml", created on Aug. 25, 2025, and having a file size of 41,263 bytes, is incorporated by reference herein.

TECHNICAL FIELD

The present invention relates to the technical field of molecular biology, and in particular, to an anti-CD40 single-domain antibody, and a preparation method therefor and use thereof.

BACKGROUND

CD40 is a 48-kDa type I transmembrane protein and acts as a critical mediator of immune cell communication in bridging innate and adaptive immunity. CD40 is found not only on hematopoietic cells such as platelets, B cells, and myeloid cells but also on non-hematopoietic cells such as endothelial cells, fibroblasts, smooth muscle cells, and even on some types of tumor cells. The cognate ligand of CD40 is CD154 (TNFSF5/CD40L), a 39-kDa type II transmembrane protein. The expression of CD40L is usually inducible and restricted to cells of the hematopoietic system, such as platelets, granulocytes, activated T cells, activated B cells, and activated natural killer (NK) cells, but it is also weakly expressed on endothelial and smooth muscle cells.

The expression of CD40 on monocytes and their progeny macrophages and dendritic cells (DCs) as well as B cells plays an important role in immune cell function. Monocytes are innate immune precursor cells with very high plasticity. They have the ability to differentiate into multiple cell types, such as macrophages, myeloid-derived suppressor cells (MDSCs), and DCs. CD40 signaling is an important trigger of the monocyte maturation process and mainly drives differentiation into macrophages of the M1 spectrum and DCs. CD40 engagement on the surface of a DC promotes cytokine and chemokine production, induces expression of costimulatory molecules, and facilitates the cross-presentation of antigens. One of the main functions of CD40L is to enhance antigen presentation to T cells by activating DCs. This step, called "licensing", enhances the interaction of DCs with T cells by upregulation of surface proteins such as CD54 and CD86, and thus activates the latter. Given the general expression profile and biological activities of CD40, the combination of CD40 agonists with other therapeutic options has been investigated in preclinical models. The use of CD40-targeted therapies with other immunomodulators or checkpoint inhibitors has shown great potential in various cancer models. For example, preclinical studies using agonistic anti-CD40 antibodies in combination with chemotherapy or kinase inhibitors have shown promising results. In 1993, Hamers' team discovered a class of antibodies with only heavy chain dimers, mainly including IgG2 and IgG3 subclasses, in the blood of camelid species (camels, dromedaries, and llamas). These antibodies lack light chains, so they are called heavy chain only like antibodies (HCAbs). Since their antigen-binding sites consist of a single variable domain called VHH, they are also called single-domain antibodies (sdAbs).

These antibodies, as variable region sequences after removing constant regions, with a molecular weight of only 15 kDa and a diameter of approximately 10 nanometers, are also called single-domain antibodies. The first constant heavy chain domain (CH1) of these HCAbs cannot be expressed possibly due to genomic mutations and deletions, causing the expressed heavy chain to lack CH1 and thus lack the capability to bind to a light chain, thereby forming a heavy chain dimer. Compared with conventional antibodies, single-domain antibodies are comparable in affinity to their scFv counterparts but perform better in stability and antigen-binding affinity, and can interact with protein clefts and active sites of enzymes. Therefore, single-domain antibodies can provide new ideas for designing small-molecule inhibitors of enzymes from mimetic peptide drugs. Since they have only heavy chains, they are easier to manufacture than monoclonal antibodies. Single-domain antibodies' unique properties, such as their stability in extreme temperature and pH environments, enable low-cost mass manufacturing. Therefore, single-domain antibodies have great value and development prospects in disease diagnosis and treatment.

Common technologies for manufacturing single-domain antibodies include phage display, biopanning, etc., among which the phage display technology requires the packaging and panning of phages and is performed in a prokaryotic expression system, with advantages of low cost, low technical difficulty, and ease of operation.

SUMMARY

The present invention provides an anti-CD40 single-domain antibody, and a preparation method therefor and use thereof. The present invention uses a PCR method to directly introduce gene fragments into eukaryotic cells and then have them expressed for subsequent assays, thereby reducing the high cost of replacing eukaryotic vectors and also saving time.

To achieve the above technical effects, the present invention employs the following technical solution:

an anti-CD40 single-domain antibody, including framework regions and complementarity determining regions (CDRs), where the CDRs include CDR1, CDR2, and CDR3; the CDR1 is SEQ ID NO. 1, the CDR2 is SEQ ID NO. 2, and the CDR3 is SEQ ID NO. 3; or, the CDR1 is SEQ ID NO. 4, the CDR2 is SEQ ID NO. 5, and the CDR3 is SEQ ID NO. 6; or, the CDR1 is SEQ ID NO. 1, the CDR2 is SEQ ID NO. 7, and the CDR3 is SEQ ID NO. 8; or, the CDR1 is SEQ ID NO. 9, the CDR2 is SEQ ID NO. 10, and the DR3 is SEQ ID NO. 11; or, the CDR1 is SEQ ID NO. 12, the CDR2 is SEQ ID NO. 13, and the CDR3 is SEQ ID NO. 14; or, the CDR1 is SEQ ID NO. 12, the CDR2 is SEQ 1D NO. 15, and the CDR3 is SEQ ID NO. 16; or the CDR1 is SEQ ID NO. 17, the CDR2 is SEQ ID NO. 18, and the CDR3 is SEQ ID NO. 19; or, the CDR1 is SEQ ID NO. 42, the CDR2 is SEQ ID NO. 20, and the CDR3 is SEQ ID NO. 21.

TABLE 1

| Amino Acid Sequences of Variable Regions of the Single-domain antibody of the Present Invention | | | |
| --- | --- | --- | --- |
| Clone No. | CDR1 | CDR2 | CDR3 |
| ANb24-Alpaca1-4M-2SP-149 | IYAIG (Sequence 1) | CITGSGSSTRYAH SVTG (Sequence 2) | ARLLSRLCVPSPD FES (Sequence 3) |
| ANb24-Alpaca1-4M-2SP-175 | YVPIG (Sequence 4) | CIIPTGITRNADSV KG (Sequence 5) | ARLLSTSCVQTSD A (Sequence 6) |
| ANb24-Abpaca1-4M-2SP-180 | IYAIG (Sequence 1) | CITGSGSSTRYAD SVTG (Sequence 7) | ARLLSMLCVPSPD FES (Sequence 8) |
| ANb24-Alpaca1-4M-2SP-226 | YYSIG (Sequence 9) | CISGGGVQRYADS AEG (Sequence 10) | ARLLMRGCAPMD NY (Sequence 11) |
| ANb24-Alpaca1-4M-2SP-273 | YYAIG (Sequence 12) | CISGSGGSTRYAD SVTG (Sequence 13) | ARLLSRLCVPSAD FDS (Sequence 14) |
| ANb24-Alpaca1-4M-2SP-317 | YYAIG (Sequence 12) | CIIGSGGSTRYFDS VLG (Sequence 15) | VRLLSRLCVPSSD FDS (Sequence 16) |
| ANb24-Alpaca1-4M-2SP-332 | SYAIG (Sequence 17) | CISGSGGSTRAAD SVQG (Sequence 18) | VRLLSRGCVPSPD FDS (Sequence 19) |
| ANb24-Alpaca1-4M-2SP-335 | YYTIG (Sequence 9) | CITAAGVPRNADS AKG (Sequence 20) | ARLLSTSCAPMND Y (Sequence 21) |

The anti-CD40 single-domain antibody has an amino acid sequence selected from any one of the following: ANb24-Alpaca1-4M-2SP-149 corresponding to SEQ ID NO. 22, ANb24-Alpaca1-4M-2SP-175 corresponding to SEQ ID NO. 23, ANb24-Alpaca1-4M-2SP-180 corresponding to SEQ ID NO. 24, ANb24-Alpaca1-4M-2SP-226 corresponding to SEQ ID NO. 25, ANb24-Alpaca1-4M-2SP-273 corresponding to SEQ ID NO. 26, ANb24-Alpaca1-4M-2SP-317 corresponding to SEQ ID NO. 27, ANb24-Alpaca1-4M-2SP-332 corresponding to SEQ ID NO. 28, and ANb24-Alpaca1-4M-2SP-335 corresponding to SEQ ID NO. 29.

The structure of the single-domain antibody of the present invention is fr-cdr1-fr-cdr2-fr-cdr3-fr, where fr represents a framework sequence, and the framework sequences are not exactly the same. For specific framework sequences, please refer to the amino acid sequence information in SEQ ID NO. 22-29.

The nucleotide sequences encoding the single-domain antibody are as follows: ANb24-Alpaca1-4M-2SP-149 corresponding to SEQ ID NO. 30, ANb24-Alpaca1-4M-2SP-175 corresponding to SEQ ID NO. 31, ANb24-Alpaca1-4M-2SP-180 corresponding to SEQ ID NO. 32, ANb24-Alpaca1-4M-2SP-226 corresponding to SEQ ID NO. 33, ANb24-Alpaca1-4M-2SP-273 corresponding to SEQ ID NO. 34, ANb24-Alpaca1-4M-2SP-317 corresponding to SEQ ID NO. 35, ANb24-Alpaca1-4M-2SP-332 corresponding to SEQ ID NO. 36, and ANb24-Alpaca1-4M-2SP-335 corresponding to SEQ ID NO. 37.

The present invention further provides a molecule expression vector, including one of the nucleotide sequences of SEQ ID NO. 30-37.

The present invention further provides a host cell containing the expression vector, where the cell is one of a mammalian cell, E. coli, and yeast, preferably a mammalian cell.

The present invention further provides a method for preparing the single-domain antibody, including:

S1: analyzing and designing, based on protein sequence and gene sequence information of CD40, an antigen that can effectively induce an alpaca to produce a specific antibody against human CD40, and connecting His-tag to its C-terminus to obtain a modified antigen;

S2: immunizing the alpaca with a mixture of the antigen obtained in the S1 and a complete Freund's adjuvant to obtain a peripheral blood mononuclear cell (PBMC) of the alpaca;

S3: extracting and reverse-transcribing ribonucleic acids (RNAs) from the PBMC obtained in the S2 into complementary deoxyribonucleic acids (cDNAs), obtaining target gene fragments through PCR, cloning the target gene fragments into a vector, and then introducing the vector into E. coli to construct an anti-CD40 VHH phage library;

S4: panning and screening an anti-CD40 single-domain antibody from the anti-CD40 VHH phage library obtained in the S3 through phage display, and performing an antigen binding assay on screened monoclonal phages to obtain CD40/His-positive clones;

S5: performing preliminary screening, eukaryotic expression and purification, and enzyme-linked immunosorbent assay (ELISA) validation on the CD40 His positive clones obtained in the S4 to obtain the anti-CD40 single-domain antibody.

Preferably, the vector described in the S3 is a p3Rdv vector.

The present invention further provides use of the single-domain antibody in preparing a type I transmembrane protein assay kit.

The present invention further provides a type I transmembrane protein assay reagent containing the anti-CD40 single-domain antibody.

The present invention further provides use of the single-domain antibody in preparing a pharmaceutical composition for cancer treatment.

Preferably, the cancer includes solid tumors and hematological tumors.

Compared with the prior art, the anti-CD40 single-domain antibody provided by the present invention has the following advantages: the single-domain antibody provided by the present invention has CD40-specific recognition and binding capabilities with strong specificity and high sensitivity, and the single-domain antibody preparation method provided by the present invention shortens antibody screening time, saves costs, and facilitates large-scale preparation of the single-domain antibody.

DETAILED DESCRIPTION OF THE EMBODIMENTS

The present invention is further explained below in conjunction with embodiments, but it should be noted that the following embodiments are only used to explain rather than limit the present invention, and all technical solutions identical or similar to the present invention fall within the protection scope of the present invention. Where no specific techniques or conditions are specified in the embodiments, operations are performed according to conventional technical methods and content of instrument specifications in the art; and where no manufacturers are specified for reagents or instruments used herein, they are all conventional products that are commercially available.

The present invention includes: constructing a CD40 antigen and immunizing an alpaca with the antigen four times to obtain a PBMC of the alpaca; using lymphocyte separation solution to separate the PBMC; treating the PBMC with Trizol to extract RNAs, obtaining antibody gene fragments through nested PCR, and cloning the fragments into a phage expression vector; constructing a phage library, and panning and screening an anti-CD40 antibody from the phage library through solid phase panning; obtaining a specific antibody through screening and sequencing result analysis; amplifying VHH fragments from unique clone bacteria through PCR, and transiently transfecting 293F cells; and finally obtaining a highly sensitive and specifically binding antibody through ELISA and cell-based binding assays after 72 h of incubation.

Example: A Method for Preparing an Anti-CD40 Antibody

S1: analyzing and designing, based on protein sequence and gene sequence information of CD40, an antigen (which may be a complete CD40 protein sequence) that can effectively induce an alpaca to produce a specific antibody against human CD40, and connecting His-tag to its C-terminus to obtain a modified antigen for subsequent purification and assays;

S2: immunizing the alpaca with a mixture of the modified antigen obtained in the S1 and a complete Freund's adjuvant four times to obtain a peripheral blood mononuclear cell (PBMC) of the alpaca;

The alpaca was initially immunized with an emulsified mixture of 200 μg of a human CD40/His protein (i.e., the modified antigen obtained in the S1) and 200 μL of the complete Freund's adjuvant, and then subjected to booster immunization with the human CD40/His protein and 200 μL of the incomplete Freund's adjuvant three times, respectively on D21, D42, and D63; one week after each time of immunization, blood was sampled for an assay of the anti-CD40/His titer in serum; one week after the fourth immunization, 50 mL of blood was sampled for phage library construction.

Figure 1:
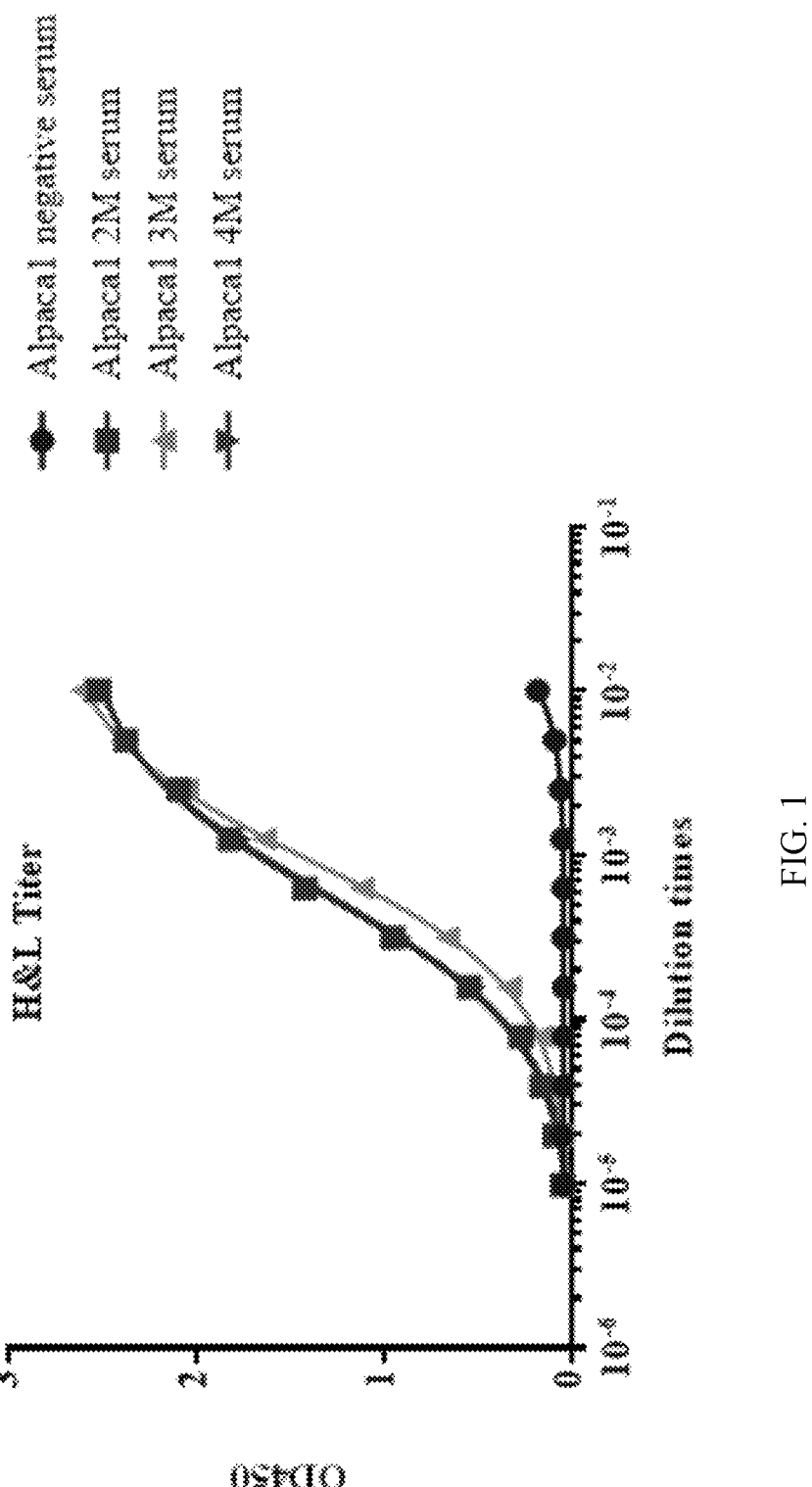
FIG. 1 shows assay results of titers in serum.

The anti-CD40/His titer in serum was analyzed by ELISA as follows: an enzyme plate was coated with the CD40/His protein at a concentration of 2 μg/mL, and 100 μL of 2-fold gradiently diluted serum was added to each well (with pre-immune alpaca serum as a control) for incubation at 37° C. for 1.5 h; after two washings, the horseradish peroxidase-labeled goat anti-alpaca IgG (H+L) secondary antibody diluted at 1:10000 was added to each well for incubation at 37° C. for 1 h; after 5 washings, 100 μL of the TMB substrate was added for incubation at 37° C. for 10 min; finally, the reaction was stopped with 50 μL of 0.1M $H_2SO_4$, and the optical density (OD) at 450 nm was measured. When the OD450 value of the sample tested was more than two times that of the negative control, the antiserum titer was determined to be positive. The results are shown in FIG. 1. For the ELISA result, a serum dilution factor that was two or more times the OD value of the blank well was selected as the titer. The results showed that the antiserum titer after 4 times of immunization was 25,600. It can be seen that the antigen can induce the alpaca to produce high-titer antiserum specifically against the CD40 protein.

Figure 2:
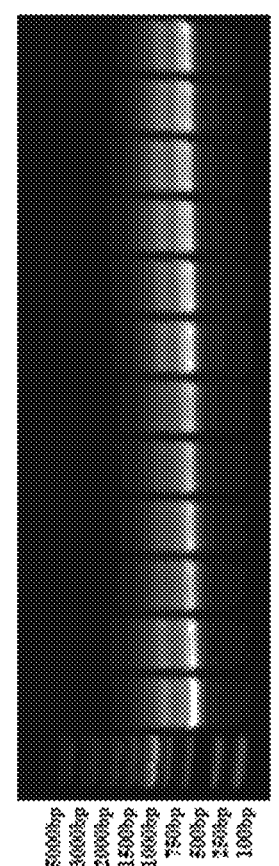
FIG. 2 shows nested PCR results.

S3: extracting and reverse-transcribing ribonucleic acids (RNAs) from the PBMC obtained in the S2 into complementary deoxyribonucleic acids (cDNAs), obtaining target gene fragments through PCR, cloning the target gene fragments into a vector, and then introducing the vector into *E. coli* to construct an anti-CD40-VHH phage library;

One week after the fourth immunization, 50 mL of blood was sampled and the PBMC was separated using lymphocyte separation solution (purchased from cytiva-Ficoll-Paque PLUS); RNAs were extracted using the Trizol method and reverse-transcribed into cDNAs using oligo (dT) (with TaKaRa-SMARTcribe Reverse Transcript as the reverse transcription kit); the target fragments were cloned into the p3Rdv vector through techniques such as nested PCR and molecular cloning, where the nested PCR system was prepared as shown in Table 2 below, with the sequence of the upstream primer DFL-01 in the system being SEQ ID NO: 38 GTTCTGACTGCTCGTC, the sequence of the downstream primer DFL-02 being SEQ ID NO: 39 CCTGCTGTCGAACTGTACC, and the amplification protocol as shown in Table 3, and the results are shown in FIG. 2 (partial results); the vector carrying the target fragments was transformed into *E. coli* competent cells to obtain an anti-CD40-VHH phage library. In order to further identify whether the anti-CD40-VHH phage library was successfully constructed, 48 clones were selected for sequencing. The sequencing results showed that the insert rate and sequence diversity were 100%, and the comparison results showed that most of the differential sequences were in the CDR binding region. It was determined after the assay that the construction resulted in an anti-CD40 VHH phage library with a capacity of 1.05E+9.

TABLE 2

| Nested PCR Amplification System | |
| --- | --- |
| Component | Usage amount |
| Q5 High-Fidelity DNA Polymerase | 0.5 μL |
| 10 mM dNTP | 1 μL |
| 5*Q5 Reaction Buffer | 10 μL |

TABLE 2-continued

| Nested PCR Amplification System | |
| --- | --- |
| Component | Usage amount |
| 5*High GC Enhancer | 10 μL |
| Upstream primer DFL-01 | 1 μL |
| Downstream primer DFL-02 | 1 μL |
| Template cDNA | 3 μL |
| ddH₂O | 23.5 μL |
| Total volume | Refilled to 50 μL |

TABLE 3

| Amplification Protocol | |
| --- | --- |
| Temperature | Time |
| 98° C. | 30 s |
| 98° C. | 10 s |
| 58° C. | 30 s |
| 72° C. | 30 s |
| 72° C. | 5 min |
| 4° C. | Thermal insulation |

S4: panning and screening an anti-CD40 single-domain antibody from the anti-CD40 VHH phage library obtained in the S3 through phage display, and performing an antigen binding assay on screened monoclonal phages to obtain CD40/His-positive clones;

The solid-phase panning method was used to coat 5 μg/mL of CD40/His (i.e., the antigen obtained in the S1) onto the ELISA plate at 4° C. overnight, 100 μL per well. After three washings with PBST, 200 μL of 2% protein-free blocking buffer (purchased from Sangon C530040-0500) was added to each well for blocking at 37° C. for 1 h. After three washings with PBST, phage (i.e. The anti-CD40-VHH phage library obtained in the S3) (approximately 2E+12 CFU) was added for incubation at 37° C. for 1 h. Unbound phage was collected by aspiration, and after 10 washings with PBST, 100 μL of glycine-hydrochloric acid (pH=2.2) solution was added to each well for reaction at 37° C. for 5 min. Then, the adsorbed phage was eluted by gentle pipetting of the plate wells, and Tris-HCl (pH=8.8) solution was added for neutralization to neutrality. The eluted phage was infected into TG1 cells in the logarithmic growth phase, and 0.5% % IPTG was added for induction on a shaking table at 30° C. for 8 h. The recovered phage was amplified and used for the next round of panning.

After three rounds of panning, Phage-ELISA was used to verify whether it was specifically enriched. Next, the ELISA plate was coated with 2 μg/mL of CD40/His at 4° C. overnight. After three washings with PBST, 3% BSA blocking buffer was added for blocking at 37° C. for 1 h. After 5 washings with PBST, the phage display library before phage display and after three rounds of panning was added for binding at 37° C. for 1 h, with about 1E+12 CFU in the first well by 4-fold gradient dilution, and the last well being blank. After 5 washings with PBST, the HRP-labeled mouse anti-M13 secondary antibody was added for incubation at 37° C. for 1 h. After 5 washings with PBST, TMB chromogenic solution was added for color development for 10 min at room temperature in the dark, and then 1M hydrochloric acid was used to terminate the color development. Finally, a microplate reader was used to read the absorbance value at a wavelength of 450 nm and a phage-ELISA binding curve was plotted.

Figure 3:
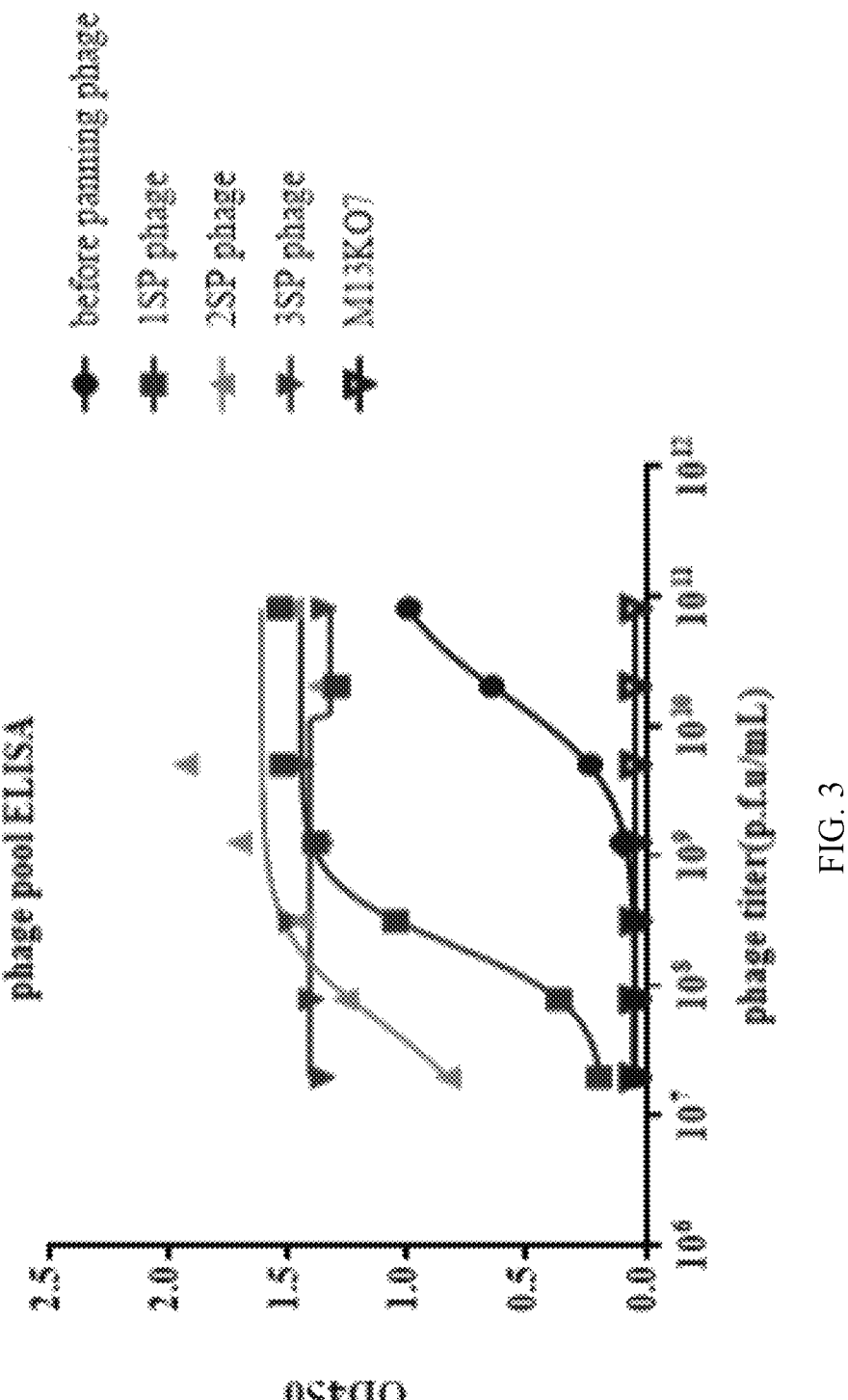
FIG. 3 shows phage pool ELISA results.

The ELISA results are shown in FIG. 3. Using the helper phage as a negative control, it can be seen from FIG. 3 that after three rounds of enrichment, the affinity of the phage group for CD40 increased round by round.

The specific process of performing an antigen binding assay on the monoclonal phages enriched in each round is as follows:

TG1 cells were infected with the enriched phage library from each round, with 264 monoclonal phages randomly selected in the first round and 528 monoclonal phages randomly selected in the second round; 0.5% % IPTG was added for induced amplification on a shaking table at 30° C. for 8 h, and the phage was recovered. Next, the ELISA plate was coated with 2 μg/mL of CD40/His at 4° C. overnight. After 3 washings with PBST, 2% protein-free blocking buffer (same as above) was added for blocking at 37° C. for 1 h; 792 amplified monoclonal phages and the helper phage as the negative control were incubated at a ratio of 1:1 with PBST solution containing 2% protein-free blocking buffer at room temperature for 1 h; the incubated phage was added to the blocked microplate and incubated at 37° C. for 1 h. After 5 washings with PBST, the HRP-labeled mouse anti-M13 secondary antibody was added for incubation at 37° C. for 1 h. After 5 washings with PBST, TMB chromogenic solution was added for color development for 10 min at room temperature in the dark, and then 1M hydrochloric acid was used to terminate the color development. Finally, a microplate reader was used to read the absorbance value at a wavelength of 450 nm. The clone was positive if the absorbance value was more than twice that of the negative control and the OD450 value was greater than 0.5. The results showed that 562 of the 792 monoclonal phages recognized CD40/His and were positive. These 562 positive clones were sequenced and analyzed to obtain 53 unique sequences.

S5: performing preliminary screening, eukaryotic expression and purification, and enzyme-linked immunosorbent assay (ELISA) validation on the CD40/His-positive clones obtained in the S4 to obtain the anti-CD40-single-domain antibody.

Preliminary screening of eukaryotic expression: the obtained 53 unique sequences were amplified by overlap PCR to amplify the VHH fragment, with the amplification system shown in Table 4, the CMV sequence being SEQ ID NO: 40 TATACGCGTTGACATTGATT, the Fc sequence being SEQ ID NO: 41 GGCCCTCACCCCAGTCAG, the F and R sequences being the same as DFL-01 and DFL-02 in the nested PCR system, and the amplification protocol shown in Table 5; the PCR product was then purified using a gel DNA recovery kit (purchased from Vazyme™, gel DNA recovery/extraction kit), and then transfected into 293F cells, and the transfected cell culture supernatant was collected for a CD40/His protein binding assay. The reagents used in the binding assay and their manufacturers are shown in Table 6. The site and function of each antibody are shown in Table 7. The monoclonal antibody-based ELISA results showed that 53 antibodies were bound to CD40/His (as shown in Table 8); after measuring the protein expression concentration in the cell culture supernatant, a cell binding ELISA was performed (as shown in Table 9).

TABLE 4

| Overlap PCR System | |
| --- | --- |
| Component | Usage amount |
| 2 x Phanta Max Master Mix | 12.5 μL |
| CMV | 0.25 μL |

TABLE 4-continued

| Overlap PCR System | |
| --- | --- |
| Component | Usage amount |
| VHH | 0.25 µL |
| Fc | 0.25 µL |
| F | 0.5 µL |
| R | 0.5 µL |
| Total volume | Refilled to 23 µL |

TABLE 6-continued

| Reagents Used in the Binding Assay and Their Manufacturers | |
| --- | --- |
| Reagent and instrument | Manufacturer/article number/batch number |
| PBS | Xi'an Heart Biotechnology/BF001 |
| Tween-20 | Sangon/A100777 |
| CD40/His | B7759/20190516A11 |
| Transiently transfected and expressed cell culture supernatant | B21107601-B21107651 |
| anti-CD40/APX005M (control antibody) | B121701/20190711A03 |
| Goat anti-human IgG-Fc, HRP | sino biologica/SSA001 |

TABLE 7

Distribution of Antibodies

| | Antibody No. | | | | | | | |
| --- | --- | --- | --- | --- | --- | --- | --- | --- |
| | 1 | 2 | 3 | 4 | 5 | 6 | 7 | 8 |
| A | ANb24-A1-4M-2SP-8 | ANb24-A1-4M-2SP-175 | ANb24-A1-4M-2SP-273 | ANb24-A1-4M-3SP-8 | ANb24-A1-4M-3SP-70 | ANb24-A1-4M-3SP-194 | ANb24-A1-4M-3SP-317 | Positive control |
| B | ANb24-A1-4M-2SP-58 | ANb24-A1-4M-2SP-180 | ANb24-A1-4M-2SP-315 | ANb24-A1-4M-3SP-10 | ANb24-A1-4M-3SP-71 | ANb24-A1-4M-3SP-262 | ANb24-A1-4M-3SP-323 | Positive control |
| C | ANb24-A1-4M-2SP-61 | ANb24-A1-4M-2SP-181 | ANb24-A1-4M-2SP-317 | ANb24-A1-4M-3SP-20 | ANb24-A1-4M-3SP-76 | ANb24-A1-4M-3SP-272 | ANb24-A1-4M-3SP-332 | Negative control |
| D | ANb24-A1-4M-2SP-106 | ANb24-A1-4M-2SP-212 | ANb24-A1-4M-2SP-332 | ANb24-A1-4M-3SP-26 | ANb24-A1-4M-3SP-83 | ANb24-A1-4M-3SP-273 | | Negative control |
| E | ANb24-A1-4M-2SP-135 | ANb24-A1-4M-2SP-221 | ANb24-A1-4M-2SP-335 | ANb24-A1-4M-3SP-33 | ANb24-A1-4M-3SP-156 | ANb24-A1-4M-3SP-275 | | Blank control |
| F | ANb24-A1-4M-2SP-149 | ANb24-A1-4M-2SP-226 | ANb24-A1-4M-2SP-352 | ANb24-A1-4M-3SP-52 | ANb24-A1-4M-3SP-182 | ANb24-A1-4M-3SP-276 | | Blank control |
| G | ANb24-A1-4M-2SP-169 | ANb24-A1-4M-2SP-260 | ANb24-A1-4M-3SP-1 | ANb24-A1-4M-3 SP-60 | ANb24-A1-4M-3SP-187 | ANb24-A1-4M-3SP-285 | | Blank control |
| H | ANb24-A1-4M-2SP-173 | ANb24-A1-4M-2SP-265 | ANb24-A1-4M-3SP-7 | ANb24-A1-4M-3SP-64 | ANb24-A1-4M-3SP-188 | ANb24-A1-4M-3SP-311 | | Blank control |

TABLE 5

| Overlap PCR Amplification Protocol | |
| --- | --- |
| Temperature | Time |
| 95° C. | 3 min |
| 95° C. | 30 s |
| 55° C. | 30 s |
| 72° C. | 1 min |
| 72° C. | 5 min |
| 4° C. | Thermal insulation |

TABLE 8

| Monoclonal Antibody-based ELISA Results | |
| --- | --- |
| Yellow fill | OD450 (positive screen plate) >0.5 |
| Purple fill | Target clone |
| Red fill | Positive control |
| Blue fill | Negative control |
| Green fill | Blank control |

TABLE 6

| Reagents Used in the Binding Assay and Their Manufacturers | |
| --- | --- |
| Reagent and instrument | Manufacturer/article number/batch number |
| Microplate | Corning ®/3590 |
| BSA | Sangon/A500023-0100 |
| TMB | Beijing Makewonderbio/1001 |
| HCl | Sinopharm/7647-01-0 |

TABLE 9

| Cell-based Binding of the Mammalian Cell Culture Supernatant and the CD40 Antigen | |
| --- | --- |
| Sample | X Mean |
| APX005M (Positive control) | 10731 |
| ANb24-A1-4M-3SP-275 | 11921 |
| ANb24-A1-4M-3SP-71 | 11748 |

TABLE 9-continued

Cell-based Binding of the Mammalian Cell
Culture Supernatant and the CD40 Antigen

| Sample | X Mean |
|---|---|
| ANb24-A1-4M-2SP-169 | 11609 |
| ANb24-A1-4M-2SP-149 | 11475 |
| ANb24-A1-4M-2SP-8 | 11247 |
| ANb24-A1-4M-3SP-1 | 11214 |
| ANb24-A1-4M-2SP-181 | 11176 |
| ANb24-A1-4M-2SP-61 | 11157 |
| ANb24-A1-4M-3SP-273 | 10862 |
| ANb24-A1-4M-3SP-262 | 10789 |
| ANb24-A1-4M-2SP-180 | 10765 |
| ANb24-A1-4M-2SP-226 | 10706 |
| ANb24-A1-4M-3SP-7 | 10608 |
| ANb24-A1-4M-2SP-175 | 10452 |
| ANb24-A1-4M-2SP-221 | 10445 |
| ANb24-A1-4M-3SP-8 | 10423 |
| ANb24-A1-4M-2SP-58 | 10383 |
| ANb24-A1-4M-2SP-173 | 10282 |
| ANb24-A1-4M-3SP-272 | 9971 |
| ANb24-A1-4M-3SP-52 | 9906 |
| ANb24-A1-4M-3SP-20 | 9752 |
| ANb24-A1-4M-3SP-317 | 9625 |
| ANb24-A1-4M-3SP-33 | 9549 |
| ANb24-A1-4M-3SP-10 | 9545 |
| ANb24-A1-4M-3SP-323 | 9497 |
| ANb24-A1-4M-2SP-260 | 9466 |
| ANb24-A1-4M-2SP-106 | 9228 |
| ANb24-A1-4M-3SP-182 | 9016 |
| ANb24-A1-4M-2SP-317 | 8971 |
| ANb24-A1-4M-2SP-335 | 8958 |
| ANb24-A1-4M-2SP-135 | 8588 |
| ANb24-A1-4M-3SP-156 | 7783 |
| ANb24-A1-4M-3SP-26 | 7683 |
| ANb24-A1-4M-3SP-194 | 7378 |
| ANb24-A1-4M-3SP-285 | 7369 |
| ANb24-A1-4M-2SP-265 | 7144 |
| ANb24-A1-4M-3SP-311 | 6908 |
| ANb24-A1-4M-3SP-60 | 6087 |
| ANb24-A1-4M-3SP-70 | 5582 |

TABLE 9-continued

Cell-based Binding of the Mammalian Cell
Culture Supernatant and the CD40 Antigen

| Sample | X Mean |
|---|---|
| ANb24-A1-4M-3SP-332 | 4829 |
| ANb24-A1-4M-3SP-64 | 4576 |
| ANb24-A1-4M-2SP-273 | 4416 |
| ANb24-A1-4M-2SP-332 | 4080 |
| ANb24-A1-4M-2SP-212 | 3996 |
| ANb24-A1-4M-3SP-187 | 2437 |
| ANb24-A1-4M-2SP-352 | 1902 |
| ANb24-A1-4M-2SP-315 | 1696 |
| ANb24-A1-4M-3SP-76 | 1412 |
| ANb24-A1-4M-3SP-188 | 1327 |
| ANb24-A1-4M-3SP-83 | 616 |
| blank | 56 |

Expression and purification of anti-CD40 monoclonal single-domain antibodies in mammalian cells: the mammalian cell expression vector pCDNA3.4 was constructed for the anti-CD40 monoclonal single-domain antibody, and then the plasmid was prepared thereby.

Figure 4:
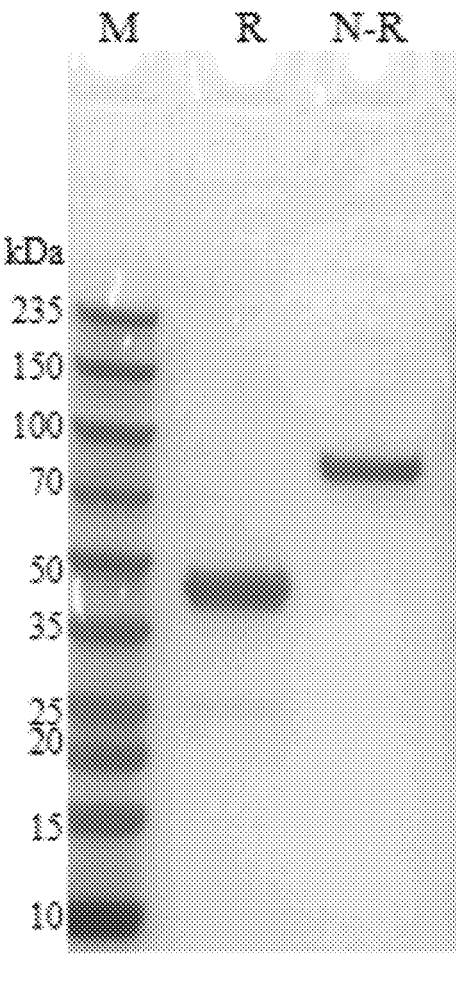
FIG. 4 is an electrophoretogram of the anti-CD40 single-domain antibody expressed in a mammalian cell.

The plasmid was transfected into the mammalian cell HEK-293 for expression for one week. The supernatant was collected and purified. The purified antibodies were collected, and the SDS-PAGE results under reducing and non-reducing conditions are shown in FIG. 4, with the reduced protein band size being 40 kDa and the non-reduced protein band size being 80 kDa. The band size was as expected.

3.7 Binding assay of the anti-CD40 monoclonal single-domain antibody using ELISA The anti-CD40 monoclonal antibody was validated using ELISA as follows: the ELISA plate was coated with 2 μg/mL of CD40/His at 4° C. overnight; 2% protein-free blocking buffer was added for blocking at 37° C. for 1 h; the anti-CD40/His monoclonal antibody was 3-fold gradiently diluted to 10 μg/mL as the first well concentration, with the last well being blank, and incubation was allowed at 37° C. for 1 h; after 5 washings with PBST, the plate was patted dry, and goat anti-human IgG-HRP as used as the secondary antibody for incubation at 37° C. for 1 h; after 5 washings with PBST, the plate was patted dry. 100 μL of TMB chromogenic solution was added to each well for color development for 10 min at room temperature in the dark, and then 2M hydrochloric acid was used to terminate the color development. Finally, a microplate reader was used to read the absorbance value at a wavelength of 450 nm.

Figure 5:
FIG. 5 shows ELISA results of the anti-CD40 single-domain antibody expressed and purified in a mammalian cell.
Figure 5:
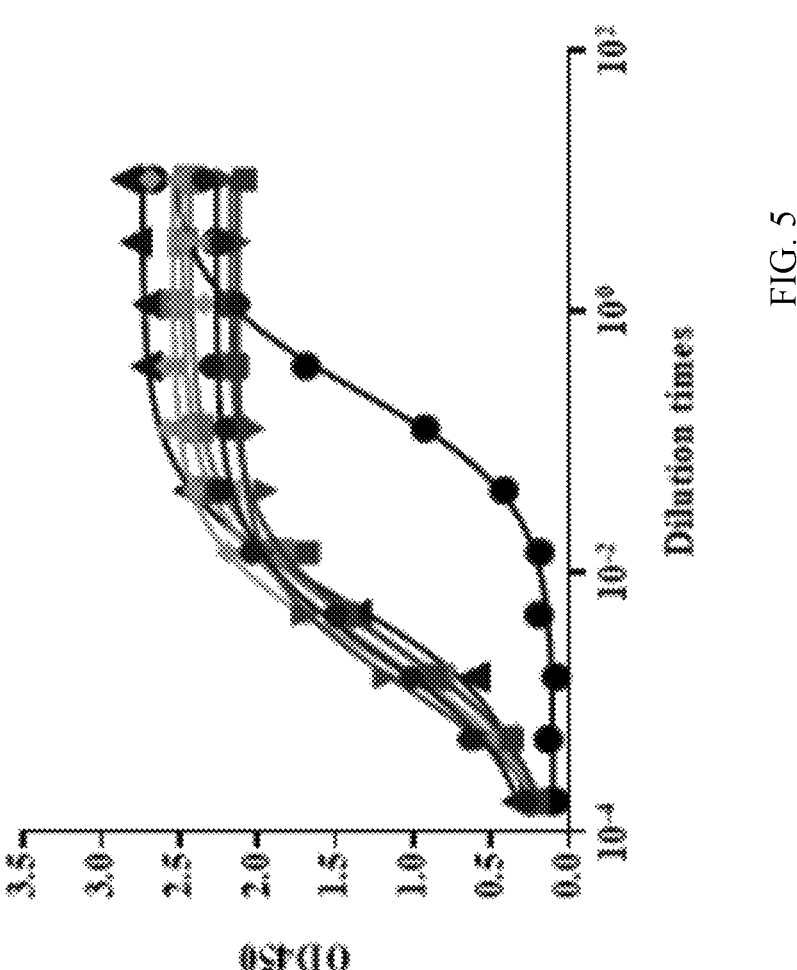

The results are shown in FIG. 5. All eight anti-CD40 monobodies could bind to CD40, and their EC50 values are shown in Table 9.

TABLE 10

| ELISA-based EC50 Values of Anti-CD40 Monobodies Expressed and Purified in Mammalian Cells | | | | | | | | |
|---|---|---|---|---|---|---|---|---|
| Antibody | ANb24-Alpacal-4M-2SP-149 | ANb24-Alpacal-4M-2SP-175 | ANb24-Alpacal-4M-2SP-180 | ANb24-Alpacal-4M-2SP-226 | ANb24-Alpacal-4M-2SP-273 | ANb24-Alpacal-4M-2SP-317 | ANb24-Alpacal-4M-2SP-332 | ANb24-Alpacal-4M-2SP-335 |
| EC50 | 0.002306 | 0.002707 | 0.002585 | 0.001254 | 0.002466 | 0.235 | 0.003195 | 0.006199 |

It can be seen from Table 9 and FIG. 5 that single-domain antibodies that can specifically bind to antigens were obtained.

Finally, it should be noted that the above embodiments are only intended to exemplarily illustrate the principle, performance, and effect of the present invention but not intended to limit the present invention. Any person of ordinary skill in the art can modify or change the above examples without departing from the spirit and scope of the present invention. Therefore, all equivalent modifications or changes made by those of ordinary skill in the art without departing from the spirit and technical ideal disclosed by the present invention should still fall within the claims of the present invention.

```
SEQUENCE LISTING

Sequence total quantity: 42
SEQ ID NO: 1              moltype = AA  length = 5
FEATURE                   Location/Qualifiers
source                    1..5
                          mol_type = protein
                          organism = synthetic construct
SEQUENCE: 1
IYAIG                                                          5

SEQ ID NO: 2              moltype = AA  length = 17
FEATURE                   Location/Qualifiers
source                    1..17
                          mol_type = protein
                          organism = synthetic construct
SEQUENCE: 2
CITGSGSSTR YAHSVTG                                             17

SEQ ID NO: 3              moltype = AA  length = 16
FEATURE                   Location/Qualifiers
source                    1..16
                          mol_type = protein
                          organism = synthetic construct
SEQUENCE: 3
ARLLSRLCVP SPDFES                                             16

SEQ ID NO: 4              moltype = AA  length = 5
FEATURE                   Location/Qualifiers
source                    1..5
                          mol_type = protein
                          organism = synthetic construct
SEQUENCE: 4
YVPIG                                                          5

SEQ ID NO: 5              moltype = AA  length = 16
FEATURE                   Location/Qualifiers
source                    1..16
                          mol_type = protein
                          organism = synthetic construct
SEQUENCE: 5
CITPTGITRN ADSVKG                                             16

SEQ ID NO: 6              moltype = AA  length = 14
FEATURE                   Location/Qualifiers
source                    1..14
                          mol_type = protein
                          organism = synthetic construct
SEQUENCE: 6
ARLLSTSCVQ TSDA                                               14

SEQ ID NO: 7              moltype = AA  length = 17
FEATURE                   Location/Qualifiers
source                    1..17
                          mol_type = protein
                          organism = synthetic construct
SEQUENCE: 7
```

-continued

```
CITGSGSSTR YADSVTG                                                    17

SEQ ID NO: 8           moltype = AA  length = 16
FEATURE                Location/Qualifiers
source                 1..16
                       mol_type = protein
                       organism = synthetic construct
SEQUENCE: 8
ARLLSMLCVP SPDFES                                                     16

SEQ ID NO: 9           moltype = AA  length = 5
FEATURE                Location/Qualifiers
source                 1..5
                       mol_type = protein
                       organism = synthetic construct
SEQUENCE: 9
YYSIG                                                                 5

SEQ ID NO: 10          moltype = AA  length = 16
FEATURE                Location/Qualifiers
source                 1..16
                       mol_type = protein
                       organism = synthetic construct
SEQUENCE: 10
CISGGGVQRY ADSAEG                                                     16

SEQ ID NO: 11          moltype = AA  length = 14
FEATURE                Location/Qualifiers
source                 1..14
                       mol_type = protein
                       organism = synthetic construct
SEQUENCE: 11
ARLLMRGCAP MDNY                                                       14

SEQ ID NO: 12          moltype = AA  length = 5
FEATURE                Location/Qualifiers
source                 1..5
                       mol_type = protein
                       organism = synthetic construct
SEQUENCE: 12
YYAIG                                                                 5

SEQ ID NO: 13          moltype = AA  length = 17
FEATURE                Location/Qualifiers
source                 1..17
                       mol_type = protein
                       organism = synthetic construct
SEQUENCE: 13
CISGSGGSTR YADSVTG                                                    17

SEQ ID NO: 14          moltype = AA  length = 16
FEATURE                Location/Qualifiers
source                 1..16
                       mol_type = protein
                       organism = synthetic construct
SEQUENCE: 14
ARLLSRLCVP SADFDS                                                     16

SEQ ID NO: 15          moltype = AA  length = 17
FEATURE                Location/Qualifiers
source                 1..17
                       mol_type = protein
                       organism = synthetic construct
SEQUENCE: 15
CIIGSGGSTR YFDSVLG                                                    17

SEQ ID NO: 16          moltype = AA  length = 16
FEATURE                Location/Qualifiers
source                 1..16
                       mol_type = protein
                       organism = synthetic construct
SEQUENCE: 16
VRLLSRLCVP SSDFDS                                                     16

SEQ ID NO: 17          moltype = AA  length = 5
FEATURE                Location/Qualifiers
source                 1..5
                       mol_type = protein
                       organism = synthetic construct
```

```
SEQUENCE: 17
SYAIG                                                                    5

SEQ ID NO: 18            moltype = AA   length = 17
FEATURE                  Location/Qualifiers
source                   1..17
                         mol_type = protein
                         organism = synthetic construct
SEQUENCE: 18
CISGSGGSTR AADSVQG                                                       17

SEQ ID NO: 19            moltype = AA   length = 16
FEATURE                  Location/Qualifiers
source                   1..16
                         mol_type = protein
                         organism = synthetic construct
SEQUENCE: 19
VRLLSRGCVP SPDFDS                                                        16

SEQ ID NO: 20            moltype = AA   length = 16
FEATURE                  Location/Qualifiers
source                   1..16
                         mol_type = protein
                         organism = synthetic construct
SEQUENCE: 20
CITAAGVPRN ADSAKG                                                        16

SEQ ID NO: 21            moltype = AA   length = 14
FEATURE                  Location/Qualifiers
source                   1..14
                         mol_type = protein
                         organism = synthetic construct
SEQUENCE: 21
ARLLSTSCAP MNDY                                                          14

SEQ ID NO: 22            moltype = AA   length = 125
FEATURE                  Location/Qualifiers
source                   1..125
                         mol_type = protein
                         organism = synthetic construct
SEQUENCE: 22
EVQLVESGGG LVQPGGSLRL SCTASGSTLD IYAIGWFRQA PGKEREGVSC ITGSGSSTRY       60
AHSVTGRFTI SRDNAKNTVF LQMNSLKPED TAVYYCAKAR LLSRLCVPSP DFESWGQGTQ       120
VTVSS                                                                    125

SEQ ID NO: 23            moltype = AA   length = 122
FEATURE                  Location/Qualifiers
source                   1..122
                         mol_type = protein
                         organism = synthetic construct
SEQUENCE: 23
QPHFVESGGG LVQPGGSLRL SCVASGFTFE YVPIGWFRQA PGKEREGVSC ITPTGITRNA       60
DSVKGRFTIS RDNAKNTVYL QLNSLKPEDT AVYYCAKARL LSTSCVQTSD ARGQGTQVTV       120
SS                                                                      122

SEQ ID NO: 24            moltype = AA   length = 125
FEATURE                  Location/Qualifiers
source                   1..125
                         mol_type = protein
                         organism = synthetic construct
SEQUENCE: 24
QPQFVESGGG LVQPGGSLRL SCTASGSTLD IYAIGWFRQA PGKEREGVSC ITGSGSSTRY       60
ADSVTGRFTI SRDNAKNTVF LQMNSLKPDD TAVYYCAKAR LLSMLCVPSP DFESWGQGTQ       120
VTVSS                                                                    125

SEQ ID NO: 25            moltype = AA   length = 122
FEATURE                  Location/Qualifiers
source                   1..122
                         mol_type = protein
                         organism = synthetic construct
SEQUENCE: 25
QLQLVESGGG LVQPGGTLRL SCAASGVTLE YYSIGWFRQS PGKEREGVSC ISGGGVQRYA       60
DSAEGRFAIS RDNAKNMVYL QMNNLEPEDT AVYYCARARL LMRGCAPMDN YWGQGTQVTV       120
SS                                                                      122

SEQ ID NO: 26            moltype = AA   length = 125
FEATURE                  Location/Qualifiers
source                   1..125
                         mol_type = protein
```

```
                              organism = synthetic construct
SEQUENCE: 26
EVQLVESGGG LVQPGGSLRL SCAASGSTLD YYAIGWFRQA PGKEREGVSC ISGSGGSTRY   60
ADSVTGRFTI SKDSAKNTVY LEMNSLKPED TAVYYCARAR LLSRLCVPSA DFDSWGQGTQ  120
VTVSS                                                             125

SEQ ID NO: 27           moltype = AA  length = 125
FEATURE                 Location/Qualifiers
source                  1..125
                        mol_type = protein
                        organism = synthetic construct
SEQUENCE: 27
QLQLVESGGD LVQPGGSLRL SCTASGHTLE YYAIGWFRQA PGKEREGVSC IIGSGGSTRY   60
FDSVLGRFTI SRDNAKNTVF LQMNSLKPED TAVYYCAKVR LLSRLCVPSS DFDSWGQGTQ  120
VTVSS                                                             125

SEQ ID NO: 28           moltype = AA  length = 125
FEATURE                 Location/Qualifiers
source                  1..125
                        mol_type = protein
                        organism = synthetic construct
SEQUENCE: 28
QVQLVESGGG LVQPGGSLRL SCAASGSTLA SYAIGWFRQA PGKEREGISC ISGSGGSTRA   60
ADSVQGRFTI SRDNAKNTVS LQMNSLKPED TAIYYCAKVR LLSRGCVPSP DFDSWGQGTQ  120
VTVSS                                                             125

SEQ ID NO: 29           moltype = AA  length = 122
FEATURE                 Location/Qualifiers
source                  1..122
                        mol_type = protein
                        organism = synthetic construct
SEQUENCE: 29
QPQFVESGGG LVQPGGTLRL SCAASGFTFE YYTIGWFRQT PGKEREGVSC ITAAGVPRNA   60
DSAKGRFTIS RDNAKNMVYL QMNNLKPEDT AVYYCAQARL LSTSCAPMND YWGQGTQVTV  120
SS                                                                122

SEQ ID NO: 30           moltype = DNA  length = 375
FEATURE                 Location/Qualifiers
source                  1..375
                        mol_type = other DNA
                        organism = synthetic construct
SEQUENCE: 30
gaggtgcagc tggtggagtc tgggggaggc ttggtgcagc ctggggggtc tctgagactc   60
tcctgtacag cctctggatc cactttggat atctatgcca taggctggtt ccgccaggcc  120
ccagggaagg agcgtgaggg ggtctcatgt attactggga gtggtagtag tacacgctat  180
gcacactccg tgacgggccg attcaccatc tccagagaca acgccaagaa cactgtgttt  240
ctgcaaatga acagcctgaa acctgaggac acggccgttt attactgtgc aaaagcgagg  300
cttctgtcca ggttatgtgt gccatcacct gactttgaat cctggggcca ggggaccag  360
gtcaccgtct cctca                                                 375

SEQ ID NO: 31           moltype = DNA  length = 366
FEATURE                 Location/Qualifiers
source                  1..366
                        mol_type = other DNA
                        organism = synthetic construct
SEQUENCE: 31
cagccgcact tcgtggagtc tggggaggc ttggtgcagc ctggggggtc tctgagactc   60
tcgtgtgtag cctctggatt cactttcgag tatgtgccga taggctggtt ccgccaggcc  120
ccagggaagg agcgtgaggg ggtctcatgt attacccta ctggtataac acgcaatgca  180
gactccgtga agggccgatt caccatctcc agagacaacg ccaagaacac agtgtatttg  240
caactgaaca gcctgaaacc tgaggacacg gccgtttatt actgtgcaaa agctaggcta  300
ctatccacct catgtgtgca gactagtgac gcccggggcc aggggaccca ggtcactgtc  360
tcctca                                                          366

SEQ ID NO: 32           moltype = DNA  length = 375
FEATURE                 Location/Qualifiers
source                  1..375
                        mol_type = other DNA
                        organism = synthetic construct
SEQUENCE: 32
cagccgcagt tcgtggagtc tgggggaggc ttggggggtc ctggggggtc tctgagactc   60
tcctgtacag cctctggatc cactttggat atctatgcca taggctggtt ccgccaggcc  120
ccagggaagg agcgtgaggg ggtctcatgt attactggga gtggtagtag tacacgctat  180
gcagactccg tgacgggccg attcaccatc tccagagaca acgccaagaa cactgtgttt  240
ctgcaaatga acagcctgaa acctgacgac acggccgttt attactgtgc aaaagcgagg  300
cttctgtcca tgttatgtgt gccatcacct gactttgaat cctggggcca ggggaccag  360
gtcactgtct cctca                                                 375

SEQ ID NO: 33           moltype = DNA  length = 366
```

```
FEATURE                 Location/Qualifiers
source                  1..366
                        mol_type = other DNA
                        organism = synthetic construct
SEQUENCE: 33
cagttgcagc tggtggagtc tggggggaggc ttggtgcagc ctggggggac tctgagactc     60
tcctgtgcag cctctggcgt cactttagag tattatagca taggctggtt ccgccagagc    120
ccagggaagg agcgtgaggg ggtctcatgt attagtggtg gtggtgtcca acggtatgca    180
gactccgcgg agggccgatt cgccatctcc agagacaacg ccaagaacat ggtgtatctg    240
caaatgaaca acctggaacc tgaggacaca gccgtttatt actgtgcacg agcccgttta    300
ctgatgaggg gatgtgcgcc aatggacaac tactgggggc aggggaccca ggtcactgtc    360
tcctca                                                                366

SEQ ID NO: 34            moltype = DNA   length = 375
FEATURE                 Location/Qualifiers
source                  1..375
                        mol_type = other DNA
                        organism = synthetic construct
SEQUENCE: 34
gaggtgcagc tggtggagtc tggggggaggc ttggtgcagc ctgggggggtc tctgagactc     60
tcctgtgcag cctctggaag cactttggat tattatgcca taggctggtt ccgccaggcc    120
ccagggaagg agcgtgaggg ggtctcatgt attagtggta gtggtggtag cacacgctat    180
gcagactccg tgacgggccg attcaccatc tccaaagaca gcgccaagaa cacggtgtat    240
ctggaaatga acagcctgaa acctgaggac acggccgttt attactgtgc acgagctaga    300
ctactgtcca ggctatgtgt gccatcagca gactttgatt cctggggcca ggggacccag    360
gtcactgtct cctca                                                      375

SEQ ID NO: 35            moltype = DNA   length = 375
FEATURE                 Location/Qualifiers
source                  1..375
                        mol_type = other DNA
                        organism = synthetic construct
SEQUENCE: 35
cagttgcagc tcgtggagtc tggggggagac ttggtgcagc ctgggggggtc tctgagactc     60
tcctgtacag cctctgggca tactttggaa tattatgcca taggctggtt ccgccaggcc    120
ccagggaagg agcgtgaggg ggtctcatgt attattggga gtggtgggag cacgcgctac    180
tttgactccg tattgggccg attcaccatc tccagagaca acgccaagaa tactgtgttt    240
ctgcaaatga acagcctgaa acctgaggac acggccgttt attactgtgc aaaagttagg    300
cttctgtcca ggctatgtgt gccatcctct gactttgatt cctggggcca ggggacccag    360
gtcaccgtct cctca                                                      375

SEQ ID NO: 36            moltype = DNA   length = 375
FEATURE                 Location/Qualifiers
source                  1..375
                        mol_type = other DNA
                        organism = synthetic construct
SEQUENCE: 36
caggtgcagc tggtggagtc tggggggaggc ttggtgcagc ctgggggggtc tctgagactc     60
tcctgtgcag cctccggatc gactttggcg tcttacgcca taggctggtt ccgccaggcc    120
ccagggaagg agcgtgaggg gatttcatgt attagtggta gtggtggtag cacacgcgct    180
gcagactccg tgcagggccg attcaccatc tccagagaca acgccaagaa cactgtgtct    240
ctgcaaatga acagcctgaa accggaggac acggccattt attactgtgc aaaagttagg    300
cttctgtcca ggggatgtgt gccatcacct gactttgatt cctggggcca gggaacccag    360
gtcaccgtct cctca                                                      375

SEQ ID NO: 37            moltype = DNA   length = 366
FEATURE                 Location/Qualifiers
source                  1..366
                        mol_type = other DNA
                        organism = synthetic construct
SEQUENCE: 37
cagccgcagt tcgtggagtc tggggggaggc ttggtgcagc ctgggggggac tctgagactc     60
tcctgtgcag cctctggatt cactttcgag tattatacca taggctggtt ccgccagacc    120
ccagggaagg agcgtgaggg ggtctcatgt attaccgctg ctggtgtccc acggaatgca    180
gactccgcga agggccgatt caccatctcc agagacaacg ccaagaacat ggtgtatttg    240
caaatgaaca acctgaaacc tgaggacaca gccgtttatt actgtgcaca gcccggttta    300
ctgtccacct catgtgcgcc aatgaacgac tactggggcc aggggaccca ggtcactgtc    360
tcctca                                                                366

SEQ ID NO: 38            moltype = DNA   length = 16
FEATURE                 Location/Qualifiers
source                  1..16
                        mol_type = other DNA
                        organism = synthetic construct
SEQUENCE: 38
gttctgactg ctcgtc                                                      16

SEQ ID NO: 39            moltype = DNA   length = 19
FEATURE                 Location/Qualifiers
```

-continued

```
source                1..19
                      mol_type = other DNA
                      organism = synthetic construct
SEQUENCE: 39
cctgctgtcg aactgtacc                                          19

SEQ ID NO: 40         moltype = DNA  length = 20
FEATURE               Location/Qualifiers
source                1..20
                      mol_type = other DNA
                      organism = synthetic construct
SEQUENCE: 40
tatacgcgtt gacattgatt                                         20

SEQ ID NO: 41         moltype = DNA  length = 18
FEATURE               Location/Qualifiers
source                1..18
                      mol_type = other DNA
                      organism = synthetic construct
SEQUENCE: 41
ggccctcacc ccagtcag                                           18

SEQ ID NO: 42         moltype = AA  length = 5
FEATURE               Location/Qualifiers
source                1..5
                      mol_type = protein
                      organism = synthetic construct
SEQUENCE: 42
YYTIG                                                          5
```

What is claimed is:

1. An anti-CD40 single-domain antibody, comprising framework regions and complementarity determining regions (CDRs), wherein the CDRs comprise CDR1, CDR2, and CDR3, respectively corresponding to SEQ ID NO. 42, SEQ ID NO. 20, and SEQ ID NO. 21 in sequence.

2. The anti-CD40 single-domain antibody of claim 1, wherein an amino acid sequence of the anti-CD40 single-domain antibody is SEQ ID NO. 29.

3. The anti-CD40 single-domain antibody of claim 1, wherein a nucleotide sequence encoding the amino acid sequence of the anti-CD40 single-domain antibody is SEQ ID NO. 37.

4. A type I transmembrane protein assay kit, comprising the anti-CD40 single-domain antibody according to claim 1 and known concentration of CD40 protein.

* * * * *